(12) United States Patent
Hubler et al.

(10) Patent No.: US 8,930,144 B2
(45) Date of Patent: Jan. 6, 2015

(54) METHOD AND APPARATUS FOR MEASURING DATA FOR INJURY ANALYSIS

(75) Inventors: Graham Hubler, Highland, MD (US); Jeffrey Byers, Fairfax, VA (US); Brian Houston, Fairfax, VA (US); Robert Corsaro, Waldorf, MD (US); Phil Frank, Laurel, MD (US); Jason Kost, Burke, VA (US); Kenny Opachko, Shantilly, VA (US); Alain Berdoz, Annandale, VA (US); Peter Herdic, Washington, DC (US); Lock-Sui Chin, Ottawa (CA); Jeffrey Levine, Nepean (CA); Jean-Philippe Dionne, Gatineau (CA); Doug Wong, Ottawa (CA); Daniel Crossman, Kanata (CA)

(73) Assignee: Med-Eng, LLC, Jacksonville, FL (US)

( * ) Notice: Subject to any disclaimer, the term of this patent is extended or adjusted under 35 U.S.C. 154(b) by 1188 days.

(21) Appl. No.: 12/746,370

(22) PCT Filed: Dec. 8, 2008

(86) PCT No.: PCT/CA2008/002124
§ 371 (c)(1),
(2), (4) Date: Dec. 20, 2010

(87) PCT Pub. No.: WO2009/070886
PCT Pub. Date: Jun. 11, 2009

(65) Prior Publication Data
US 2011/0098934 A1    Apr. 28, 2011

Related U.S. Application Data

(60) Provisional application No. 60/996,855, filed on Dec. 7, 2007.

(51) Int. Cl.
*G01P 1/12*    (2006.01)
*G06F 19/00*    (2011.01)
(Continued)

(52) U.S. Cl.
CPC   *F41H 1/04* (2013.01); *A42B 3/046* (2013.01); *A61B 5/11* (2013.01); *A61B 5/6814* (2013.01);
(Continued)

(58) Field of Classification Search
CPC .... A42B 3/046; A61B 5/6814; A61B 5/7275; A61B 5/6803; G01L 5/14
USPC .......... 702/55, 141, 131, 138, 139, 19; 2/422, 2/205, 421, 425; 73/514.01, 480; 340/669, 870.24, 807.01; 600/595
See application file for complete search history.

(56) References Cited

U.S. PATENT DOCUMENTS

| | | | |
|---|---|---|---|
| 5,978,972 A | 11/1999 | Stewart et al. | |
| 6,122,959 A | * 9/2000 | Hoshal et al. | 73/489 |

(Continued)

FOREIGN PATENT DOCUMENTS

| | | |
|---|---|---|
| WO | WO 2004/070336 | 8/2004 |
| WO | WO 2008/069682 | 6/2008 |

*Primary Examiner* — Carol S Tsai
(74) *Attorney, Agent, or Firm* — Kane Kessler, P.C.; Paul E. Szabo

(57) ABSTRACT

An apparatus as provided for measuring acceleration of a person's head or other object. The apparatus comprises a sensor for sensing acceleration and a controller for controlling recording of data resulting from the sensed acceleration due to an explosive force. The controller is adapted to determine whether or not to enable recording of the data based on the sensed acceleration. A data receiver is provided to receive the sensed acceleration data from the sensing means, and requires electrical power to enable data to be received thereby. The controller controls electrical power to the receiver so that if the sensed acceleration reaches or exceeds a predetermined value, electrical power to the data receiver is enabled. The recorded acceleration data may be used for injury analysis.

14 Claims, 11 Drawing Sheets

(51) Int. Cl.
  *G01P 15/00* (2006.01)
  *F41H 1/04* (2006.01)
  *A42B 3/04* (2006.01)
  *A61B 5/11* (2006.01)
  *A61B 5/00* (2006.01)
  *G01L 5/14* (2006.01)

(52) U.S. Cl.
  CPC . *G01L 5/14* (2013.01); *G01P 1/127* (2013.01); *A61B 5/7275* (2013.01); *A61B 2562/0219* (2013.01); *A61B 5/6803* (2013.01); *A61B 2560/0209* (2013.01)
  USPC .......... 702/19; 702/55; 702/141; 702/131; 702/138; 702/139; 2/422; 2/205; 2/421; 2/425; 73/514.01; 73/480; 340/669; 340/870.24; 340/870.01; 600/595

(56) References Cited

U.S. PATENT DOCUMENTS

| | | | |
|---|---|---|---|
| 7,526,389 B2* | 4/2009 | Greenwald et al. | 702/55 |
| 7,992,421 B2* | 8/2011 | Jeftic-Stojanovski et al. | 73/12.04 |
| 8,316,691 B2* | 11/2012 | Jeftic-Stojanovski et al. | 73/12.04 |
| 8,322,188 B2* | 12/2012 | Jeftic-Stojanovski et al. | 73/12.04 |
| 8,539,815 B2* | 9/2013 | Jeftic-Stojanovski et al. | 73/12.04 |
| 2005/0177929 A1* | 8/2005 | Greenwald et al. | 2/425 |
| 2005/0266967 A1 | 12/2005 | Considine et al. | |
| 2006/0038694 A1 | 2/2006 | Naunheim et al. | |

* cited by examiner

METHOD AND APPARATUS FOR MEASURING DATA FOR INJURY ANALYSIS

FIELD OF THE INVENTION

The present invention relates to apparatus and methods for measuring and recording data from potentially injurious events to which humans may be exposed.

SUMMARY OF THE INVENTION

Embodiments of the present invention provide a data recorder adapted for mounting on a combat helmet to measure and record parameters indicative of head acceleration resulting from violent events such as violent impact and blast events. Despite current designs of head protection, exposure of a large number of soldiers to detonation of improvised explosive devices (IEDs) has resulted in a high occurrence of blast-induced traumatic brain injuries (TBI). TBI has been noted to lead to injuries ranging from headaches and mild concussions to severe casualties including severe concussions and memory loss. The data recorder enables data from violent events to be recorded and used to build a database of head acceleration data induced by violent events which may be correlated with injuries suffered. The data recorded from violent events may be used to correlate injuries, especially brain injuries, with event characteristics and severity, including accumulated dosage and long-term and chronic symptoms. The analyzed data may be used to determine optimal medical treatment based on instant analysis of event data and/or making longer term medical decisions. The data may be used to assess effectiveness of protective equipment, both in helmet technology and other applications.

Embodiments of the data recorder provide a small, lightweight, self-contained digital recording system, capable of recording acceleration waveforms experienced in violent events. Embodiments of the data recorder are designed to mount on helmets and monitor and record exposure to potentially harmful cranial events. Embodiments of the datalogger enable both the direction and magnitude of acceleration to be measured. In some embodiments, the data recorder includes three accelerometers that are each only sensitive to accelerations in a single direction (axis). The accelerometers are mounted orthogonally to measure the vector components of acceleration in three-dimensional space. Embodiments of the data recorder enable acceleration to be measured by all three accelerometers simultaneously, with the vector sum of their signals indicating both the direction of the acceleration and the magnitude of acceleration.

Embodiments of the data recorder include a power management system for reducing the amount of power consumed by the device to extend the time over which the device can remain operational in the field. In particular, the power management system provides a means of switching part(s) of the data recorder between active and inactive states so that power required by those parts to perform a particular function is only provided when the particular function is to be performed.

Embodiments of the data recorder include a memory management scheme for managing the recording of data and which is capable of deciding which data to save and which to discard in order to reduce the amount of memory space required, and also how to use the available memory space to store the data efficiently and reduce power.

According to one aspect of the present invention, there is provided an apparatus for measuring acceleration of a person's head or other object, comprising sensing means for sensing acceleration, and a controller for controlling recording of data resulting from the sensed acceleration, wherein the controller is adapted to determine, based on the sensed acceleration, whether or not to enable recording of the data.

In some embodiments, the controller is adapted to enable recording of the data if the sensed acceleration meets a predetermined criteria, for example, if the measured acceleration reaches or exceeds a predetermined value. The predetermined or threshold value may be a finite value below a value that would or is likely to cause a predetermined injury to a person.

Some embodiments may be adapted to base the determination on any other characteristic of the sensed acceleration, for example, a time derivative of acceleration such as the slope of an impulse or Fourier frequency component(s) in the waveforms. This may enable even earlier detection of significant events.

In some embodiments, the apparatus comprises data receiving means for receiving sensed acceleration data from the sensing means, the receiving means requiring electrical power to enable the data to be received thereby, and wherein the controller causes electrical power to the receiving means to be controlled based on the sensed acceleration.

In some embodiments, the controller is adapted to determine whether or not the sensed acceleration meets a predetermined criteria, and if the criteria is not met, the controller causes the electrical power to be controlled such that the receiving means is unable to receive the data. On the other hand, if the criteria is met, the controller is adapted to cause the electrical power to be controlled to enable the receiving means to receive the data.

Advantageously, the predetermined threshold value may be selected to provide sufficient time for the receiving means to change from an inactive state to an active state to receive acceleration data indicative of an injury.

In some embodiments, the receiving means comprises any one or more of signal conditioning means for conditioning the signal, an analog-to-digital converter, a processor and a memory. The memory may comprise a volatile memory such as a random access memory.

Embodiments of the apparatus may further comprise a second memory operatively coupled to the first memory for receiving data therefrom. The second memory may comprise a non-volatile memory or another memory requiring no power or less power than the first memory to hold data.

In some embodiments, the apparatus further comprises determining means for determining whether or not to transfer data from the first memory to the second memory. The determination may be based on the acceleration data. The determining means may be adapted to cause the data to be transferred from the first memory to the second memory, if the acceleration data meets a predetermined criteria. The predetermined criteria may be, for example, that a value of acceleration in the acceleration data (which may or may not be the peak acceleration) is likely to be sufficient to cause injury or has been previously determined to cause injury. At least one of the first and second memories may be an internal memory of a processor.

In some embodiments, the apparatus further comprises a third memory operatively coupled to the second memory for receiving data therefrom. A memory controller may be provided for controlling the transfer of data from the second memory to the third memory. The memory controller may be conditioned to transfer acceleration data from the second and third memory only if the second memory contains acceleration data from a plurality of separate events.

In some embodiments, the memory controller is adapted to transfer acceleration data relating to a plurality of different events from the second to the third memory in a single or the same write operation. Advantageously, this transfer scheme assists in reducing power since write operations can be power intensive. For example, the memory controller may be adapted to transfer acceleration data relating to three or more events in a single operation, for example, 5, 10, 15 or 20 or any other number.

In some embodiments, the apparatus further comprises monitoring means for monitoring the time of an acceleration event and means for recording acceleration data of an event and the time of the event. Advantageously, this arrangement allows acceleration data to be time stamped so that it can be correlated with other information that may be recorded about the event and which may assist in the compilation and analysis of injury data.

The acceleration sensor may be adapted to sense acceleration from an explosive force, and may for example, be capable of measuring forces of 1,500 gs or more, 5,000 gs or more, 10,000 gs or more or 15,000 gs or more.

In some embodiments, the data recording means is capable of recording acceleration waveforms having frequencies in the range of at least 500 to 1,000 Hz, or more.

In some embodiments, the data recording means is capable of changing from an inactive state to an active state in less than 1 millisecond, for example, less than 500 microseconds or less than 400, 300 or 200 microseconds, or in about 100 microseconds or less.

In some embodiments, the apparatus further comprises monitoring means for monitoring a power source for providing power to the apparatus.

In some embodiments, the apparatus further includes a temperature sensor for sensing the temperature of one or more components of the apparatus. As components of the data recorder, for example, the sensors, may be temperature dependent, measuring the temperature may assist in performing temperature compensation and increasing the accuracy of the measurements, where needed.

The data recorder may be adapted to be mounted to a helmet, for example, to the helmet shell, for example on the outside of the shell. The data recorder may be adapted for releasably fastening to the helmet so that it can be readily removed therefrom and replaced, as necessary.

According to another aspect of the present invention, there is provided an apparatus for measuring a parameter resulting from exposure of a person to a physical event, comprising sensor means for sensing said parameter, determining means for determining a relationship between the value of the sensed parameter and a predetermined value of said parameter, and a controller responsive to the determining means for controlling a device in response to the determination made by the determining means.

According to another aspect of the present invention, there is provided an apparatus for measuring acceleration of a person's head resulting from exposure of the head to a force, the apparatus comprising sensing means for sensing said acceleration, determining means for determining a relationship between the value of the sensed acceleration and a predetermined value of acceleration, and a controller responsive to said determining means for controlling a device in response to the determination made by the determining means.

In some embodiments, the sensing means comprises an accelerometer for measuring acceleration in three mutually orthogonal directions.

In some embodiments, the relationship determined by said determining means is whether or not the sensed value of acceleration is equal to or exceeds the predetermined value.

In some embodiments, the predetermined value is below a value determined to cause a predetermined degree of injury.

In some embodiments, the device comprises a power controller, a memory, a processor, an indicator or another device.

In some embodiments, the device comprises a recording means for recording the value of the sensed parameter.

In some embodiments, the apparatus includes mounting means for mounting the apparatus to a protective helmet.

Advantageously, the apparatus allows head acceleration to be measured only when it is determined that the sensed acceleration is sufficient to actually warrant recording the measurement thereby reducing the electrical power requirements and extending the useful life of the system when powered by a battery.

According to another aspect of the present invention, there is provided an apparatus for recording data indicative of acceleration of a part of a person's body or other object, comprising first memory means for receiving acceleration data from an acceleration sensor, second memory means operatively coupled to the first memory means for receiving data from the first memory means, and a data transfer controller for controlling the transfer of data from the first memory means to the second memory means based on the acceleration data.

According to another aspect of the present invention, there is provided a method of calibrating a data recording unit for measuring head acceleration, comprising the steps of: (a) providing a data recording unit mounted to a head protector; (b) mounting the head protector on a support; (c) subjecting the head protector to a force or change in pressure; (d) measuring acceleration of the head protector resulting from the force or change in pressure; (e) measuring acceleration of the support resulting from the force or change in pressure; and (f) determining a relationship between the measured acceleration of the head protector and the support.

According to another aspect of the present invention, there is provided a method of determining the value of a parameter indicative of acceleration of a person's head, comprising the steps of: acquiring data measured by an acceleration sensor mounted to a head protector and using a calibration method to determine from the data the value of said parameter.

According to another aspect of the present invention, there is provided a method of monitoring acceleration of a part of a body of military or service personnel comprising mounting a monitor for monitoring acceleration to the body part to be monitored.

Embodiments of the method may include any one or more additional features disclosed herein.

BRIEF DESCRIPTION OF THE DRAWINGS

Examples of embodiments of the present invention will now be described with reference to the drawings, in which.

DETAILED DESCRIPTION

Figure 1:
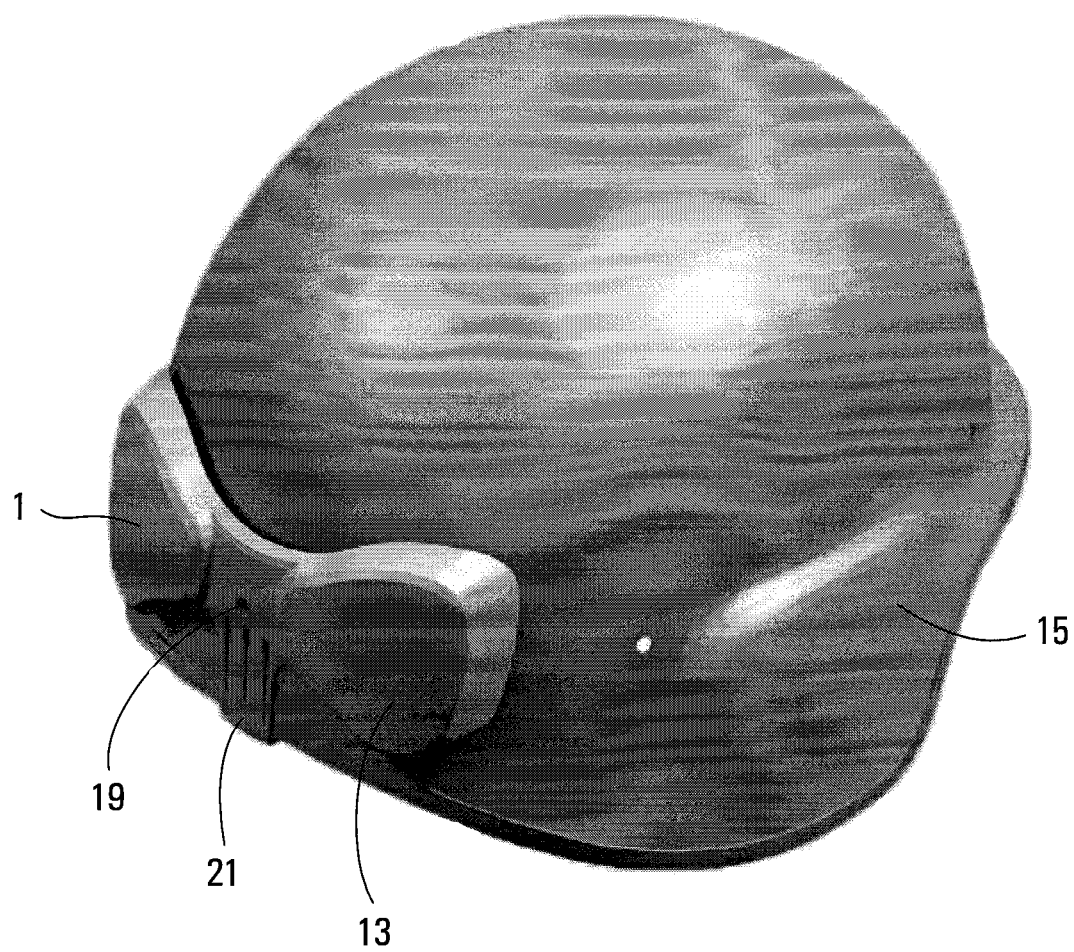
FIG. 1 shows a front perspective view of a data recording unit according to an embodiment of the present invention, mounted to the rear of a military helmet.
Figure 2:
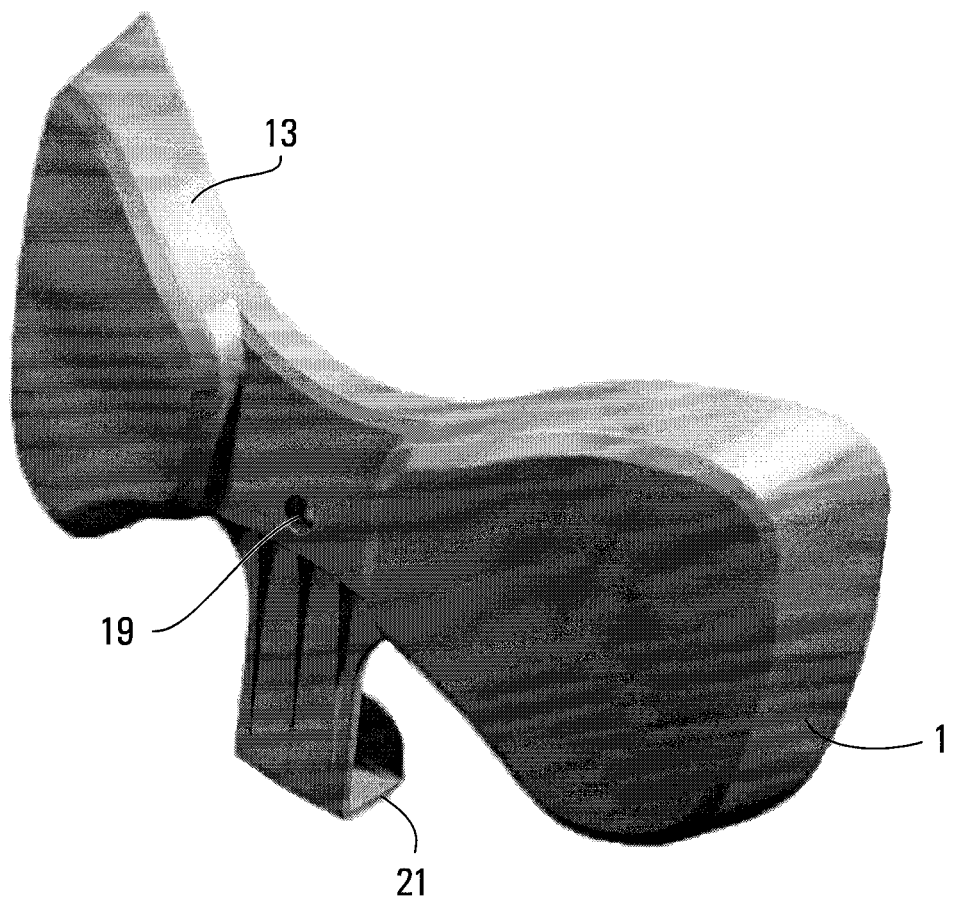
FIG. 2 shows a front perspective view of the data recording unit of FIG. 1 in more detail.
Figure 3:
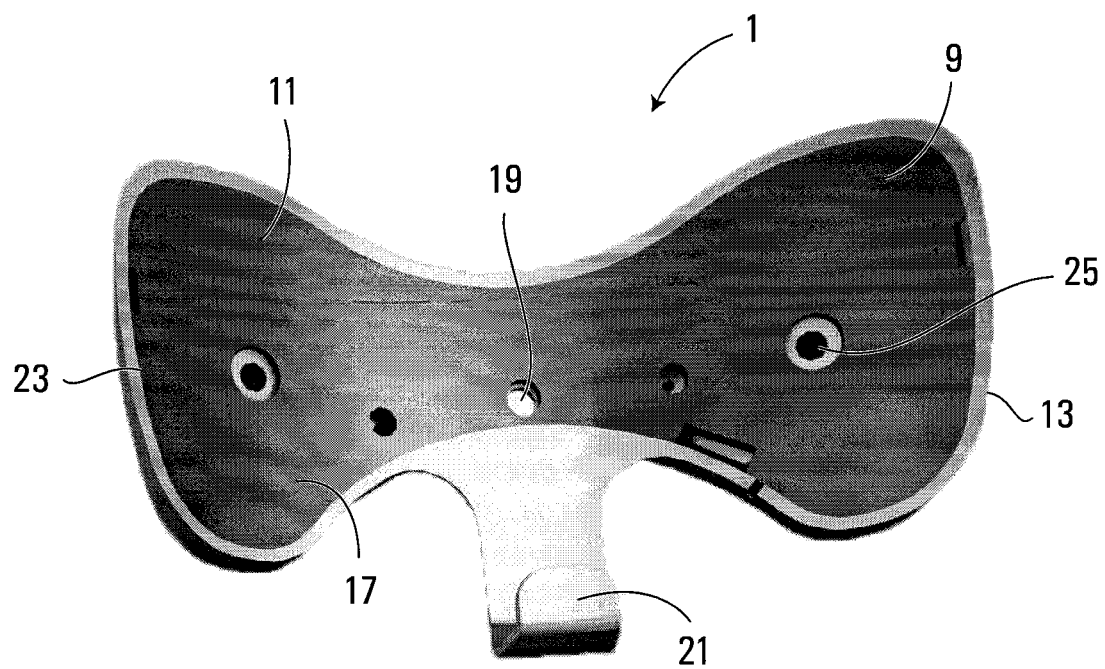
FIG. 3 shows a rear perspective view of the data recording unit shown in FIGS. 1 and 2.
Figure 4:
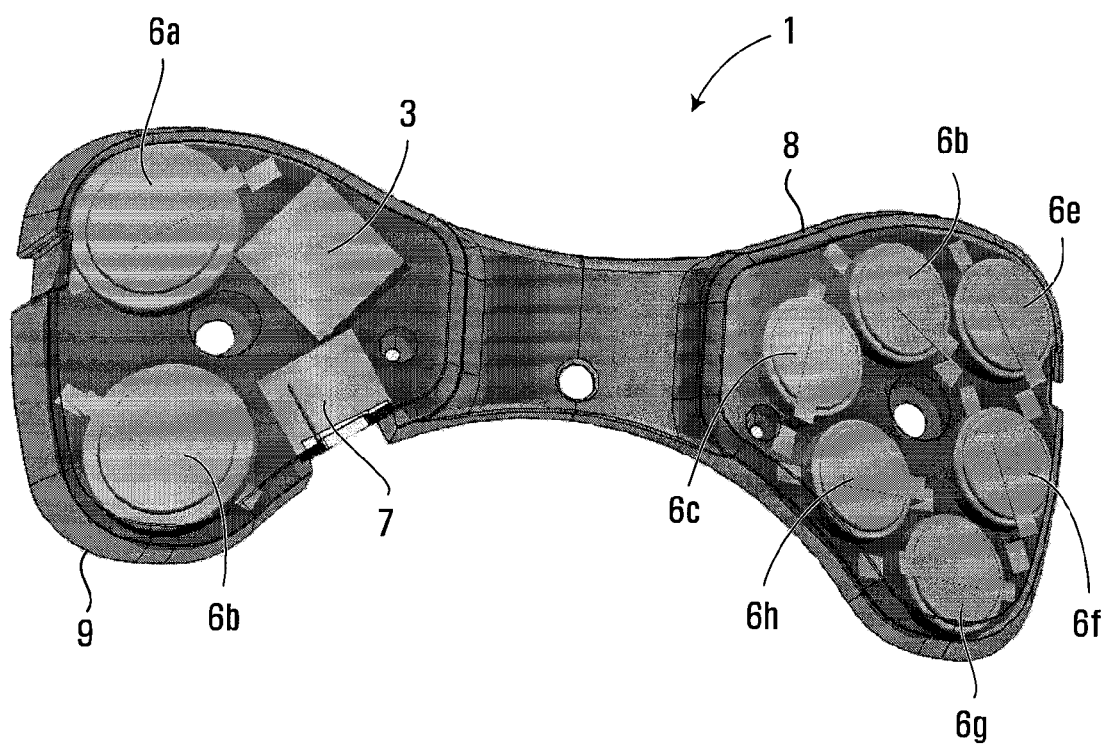
FIG. 4 shows a semi-transparent view of some of the circuitry of the data recording unit of FIGS. 1 to 3.
Figure 5:
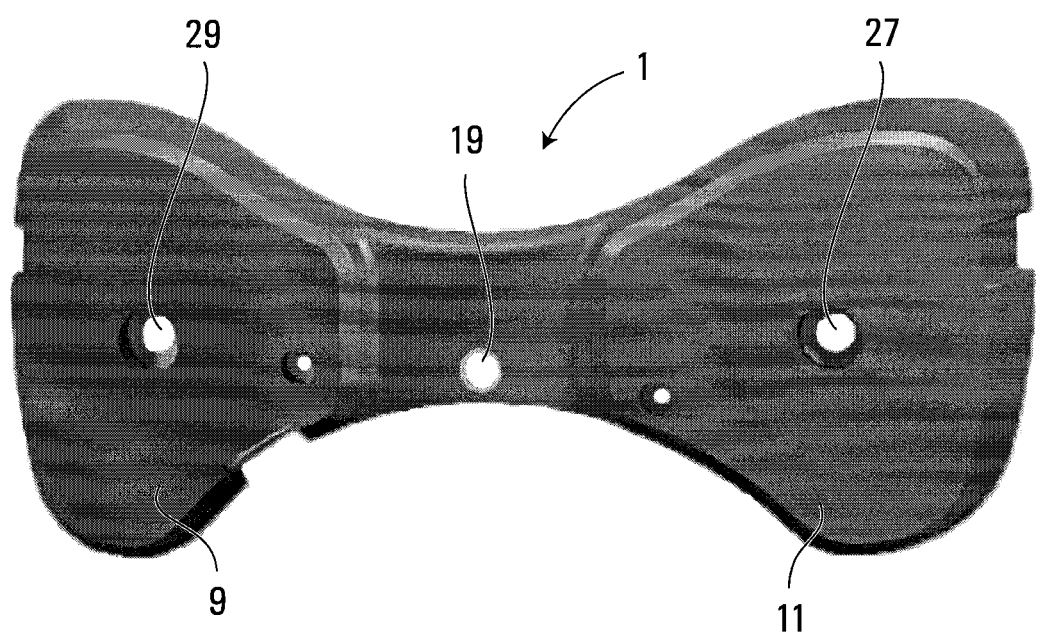
FIG. 5 shows a front perspective view of the data recording unit encapsulated in a mold.
Figure 6:
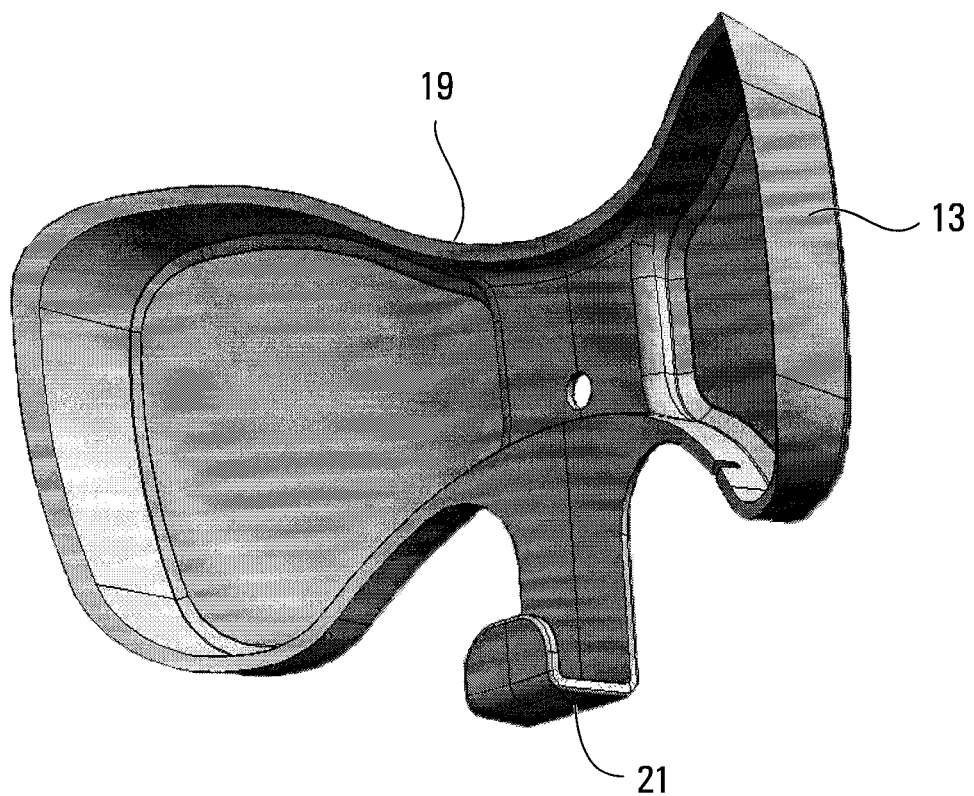
FIG. 6 shows a rear perspective view of a molded cover for the data recording unit.

Referring to FIGS. 1 to 7, a data recording unit 1 according to an embodiment of the present invention comprises a sensor 3 for sensing acceleration, and circuitry 5 (FIG. 7) for recording acceleration data. The unit includes a source 6 of electrical power, which may comprise one or more battery cells, for example, cells 6a to 6h, which may be standard "coin" cells. A communication port 7 may be provided for connection to and/or communication with an external device. Components of the data recording unit may be mounted on a circuit card assembly 8 which may be subsequently encapsulated in an epoxy mold 9 to form an integral unit 11. A cap 13 is provided to cover the front and peripheral edge of the unit and the unit and cap are mounted on a protective helmet 15, as shown in FIG. 1. In this embodiment, the rear face 17 of the unit generally conforms to the shape of the part of the helmet against which it is mounted. The unit may be designed to be mounted on the rear part of a helmet, although in other embodiments, the unit may be mounted on any other part of the helmet. A through hole 19 is provided through the unit and cap for receiving a mounting bolt or screw to secure the unit to the helmet shell. The through hole may be positioned to coincide with the position of an existing through hole in the helmet, for example, for mounting the internal suspension system, avoiding the need for making any additional holes in the helmet which might compromise its protective performance. In this embodiment, the unit includes a clip 21 which is adapted to clip under the lower peripheral edge of the helmet to assist in retaining the unit to the helmet, and may be integrally formed with the cap. In other embodiments, the clip may be integrally formed with the epoxy layer or mold, or may comprise a separate piece. In this embodiment, the cap is provided with internal projections 23, 25 which register with corresponding apertures 27, 29 formed in the unit 11 to assist in locating the cap on the unit and preventing relative movement between the two.

In other embodiments, alternative or additional fastening means may be provided to securely fasten the data recording unit to the helmet.

The data recording unit comprises an acceleration sensor, discrimination circuitry for determining whether or not the measured acceleration is at or exceeds a predetermined value, and circuitry responsive to the discrimination circuitry for recording measured values of acceleration.

Figure 7:
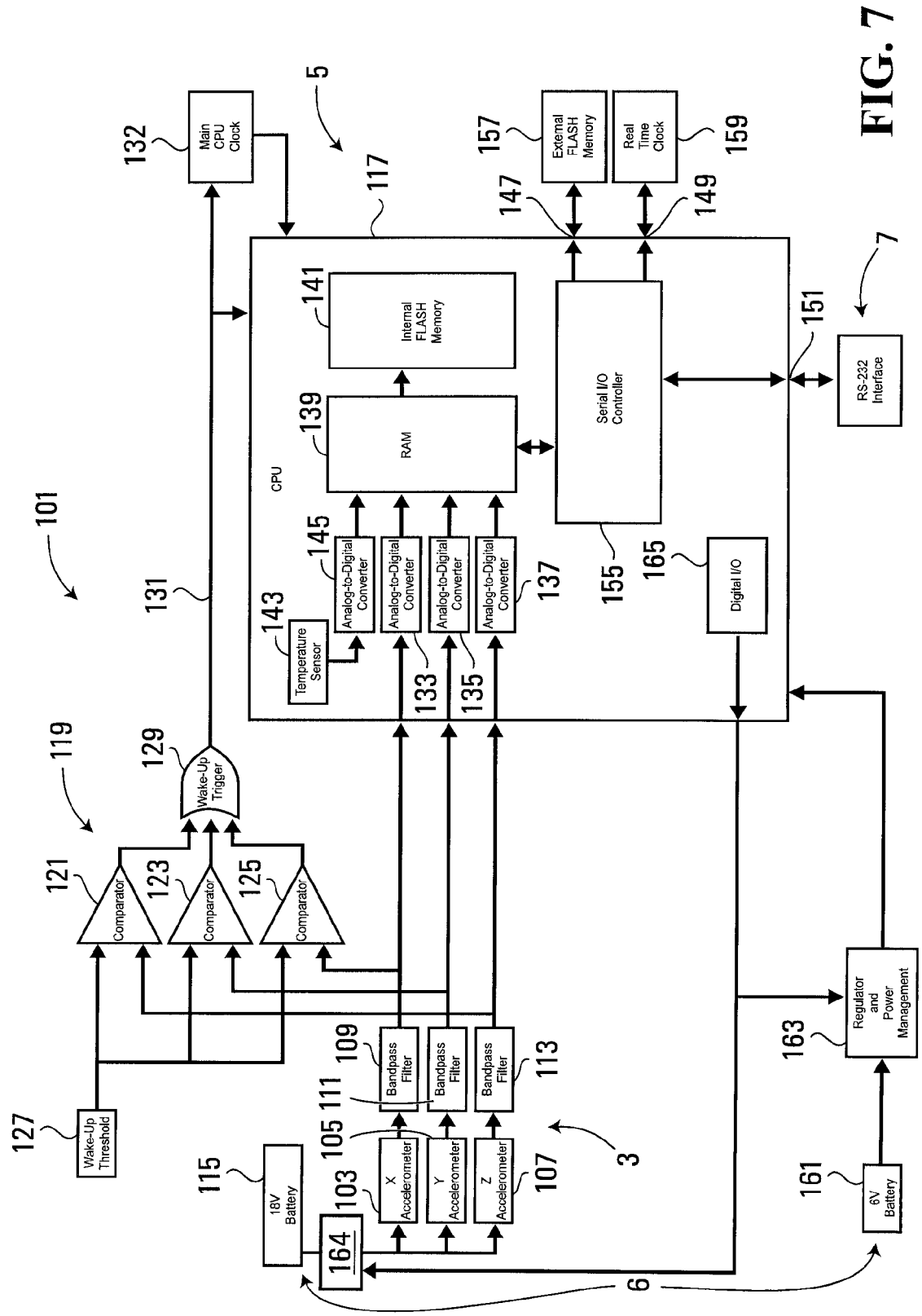
FIG. 7 shows a block diagram of components of a data recording unit according to an embodiment of the present invention.

A block diagram of an example of a data recording unit is shown in FIG. 7. Referring to FIG. 7, the data recording unit 101 includes first, second and third accelerometers 103, 105, 107, each of which measures acceleration in a single direction which is orthogonal to the acceleration direction measured by the other two accelerometers. The accelerometers may be arranged so that they each lie on a respective one of three mutually orthogonal axes in which all of the axes meet at a common point, to assist in resolving the actual direction of acceleration from the acceleration trace produced by each accelerometer. In this embodiment, the first accelerometer 103 measures acceleration in the front-back (designated x) direction, the second accelerometer 105 measures acceleration in the left-right (designated y) direction, and the third accelerometer 107 measures acceleration in the up-down (designated z) direction. In some embodiments, the accelerometers use transducers that produce or generate an electrical signal in response to sensing acceleration, without the transducers requiring electrical power to do so, in order to help reduce power requirements. In some embodiments, the accelerometers use transducers that exploit the Piezo-electric effect to generate a charge whose value varies with acceleration and may be proportional to acceleration, for example.

A respective band pass filter 109, 111, 113 may be provided for filtering the signal from each accelerometer 103, 105, 107. A respective amplifier (not shown) may be provided to amplify each accelerometer signal, either before or after the band pass filter, or both. In some embodiments, the amplifiers may be very low power op-amps to help minimize the amount of power required by the sensor circuitry. Electrical power for the sensor circuitry is provided by a suitable power source 115, which may comprise one or more individual battery cells.

The data recording unit includes a data processing unit 117 for receiving acceleration signals from the accelerometers 103, 105, 107, and a control or discriminating circuit 119 for controlling the state of the data processing unit 117 to manage the power drawn by the unit. In particular, the control circuit 119 is arranged to control the data processing unit 117 between a first, inactive state in which the data processing unit is in "sleep" mode and draws no or little power and is unable to record acceleration data, and a second state in which the data processing unit is in "an awake" mode or active state and able to record acceleration data. In this embodiment, the control circuit 119 comprises a respective comparator 121, 123, 125 coupled to receive acceleration signals from a respective accelerometer and for comparing the magnitude of the acceleration signals with a predetermined value. In this particular embodiment, one input of each comparator is coupled to receive a respective accelerometer signal from a respective band pass filter and another input of each comparator is coupled to receive the threshold value provided by a suitable source 127. The output of each comparator is coupled to a suitable logic device or circuit, for example, an OR gate 129 which is arranged to output a trigger signal 131 to the data processor unit 117 to cause the data processing unit to change from an asleep state to an awake state if the acceleration measured by any one of the accelerometers reaches or exceeds the predetermined threshold value. A main clock 132 provides clocking signals to the data processing unit, and, in this embodiment, is an external clock, although in other embodiments, the clock may be internal of the CPU. The trigger signal 131 is provided to the main clock 132 to control operation thereof, as described in more detail below.

Some embodiments may be adapted to base the determination as to whether or not to enable the data recording unit to receive and record acceleration data on any other characteristic of the sensed acceleration. These may include any one or more of a time derivative of acceleration, such as the slope of an impulse, or Fourier frequency component(s) in the waveforms. A derivative circuit may be provided to monitor the slopes of impulses, or appropriate circuitry may be provided to perform a Fourier analysis on the waveform, and to determine whether the resulting values meet a predetermined criteria. This may allow even earlier detection of significant events.

The data processing unit 117 includes first, second and third analog-to-digital converters 133, 135, 137 for receiving acceleration signals from a respective accelerometer 103, 105, 107, a first memory unit 139 for recording digital acceleration data from each A to D converter 133, 135, 137, and a second memory unit 141 for receiving data from the first memory unit 139. The first memory unit may comprise a volatile memory, e.g. a random access memory (RAM) and the second memory unit may comprise a non-volatile memory, for example, a FLASH memory. The data processing unit 117 may also include a temperature sensor 143 and possibly a fourth analog to digital converter 145 for receiving an analog signal indicative of temperature from the temperature sensor and passing a corresponding digital signal to the first memory unit 139 to be recorded therein. The data processing unit also includes one or more interface(s) 147, 149, 151 for communicating and exchanging signals with one or more external device(s), and an I/O controller 155 for controlling the transfer of data between internal memory of the data processing unit 117 and external device(s).

The data recording unit includes an external memory 157 and a real time clock 159 coupled to a respective interface 147, 149 of the data processing unit 117 and which are capable of communicating with its internal memory 139 via the I/O controller 155. The real time clock provides an indication of real time (e.g. including any one or more of year, month, day and time, (e.g. hour, and optionally minute and optionally second) and enables event data to be time-stamped. Time-stamping enables the event to be correlated with other information or record(s) of an event. One of the interfaces of the data processing unit 151 includes a general interface port adapted for releasable connection to a peripheral device, such as a host computer. In the present embodiment, the interface 155 is an RS-232 interface, although in other embodiments, the interface 151 may comprise any other suitable interface, for example, a USE.

The data recording unit also includes a power source 161 for providing electrical power to the data processing unit. Regulator and power management modules 163, 164 are provided for regulating power to the data processing unit and the acceleration sensor circuitry, respectively. In this particular embodiment, the regulator and power management modules 163, 164 are coupled to a interface 165 (e.g. a digital I/O interface) of the data processing unit. In some embodiments, the regulator and power management modules 163, 164 may each comprise a switch, which switchably couples/decouples the power sources to/from the data processing unit 117 and sensor circuitry in response to a control signal from the interface 165. Each power management module may be controlled independently of the other, or may be controlled together, for example using the same control signal. The switch may enable the respective power sources to be completely disconnected from their associated circuitry (load), so that substantially no power is drawn when the unit is in storage, for example.

Power Management

Embodiments of the data recording unit are designed to operate continuously for extended periods of time using stored electrical energy from a battery, for example, without any requirement for recharging, and the associated infrastructure, or replacing the battery. Some embodiments are designed to operate continuously for the duration of a typical "tour of duty" for military personnel which may last for up to six months, or more. In normal operation, i.e. in the absence of exposure to a violent event, components which are required to record data are maintained in an "off" or inactive state where little or no power is drawn by those components. In this state, only the acceleration sensors, their associated circuitry (i.e. op-amps and band pass filters) and the control circuit 119 are active. In some embodiment, the comparators 121, 123, 125 of the control circuit are selected to draw little power.

Figure 8:
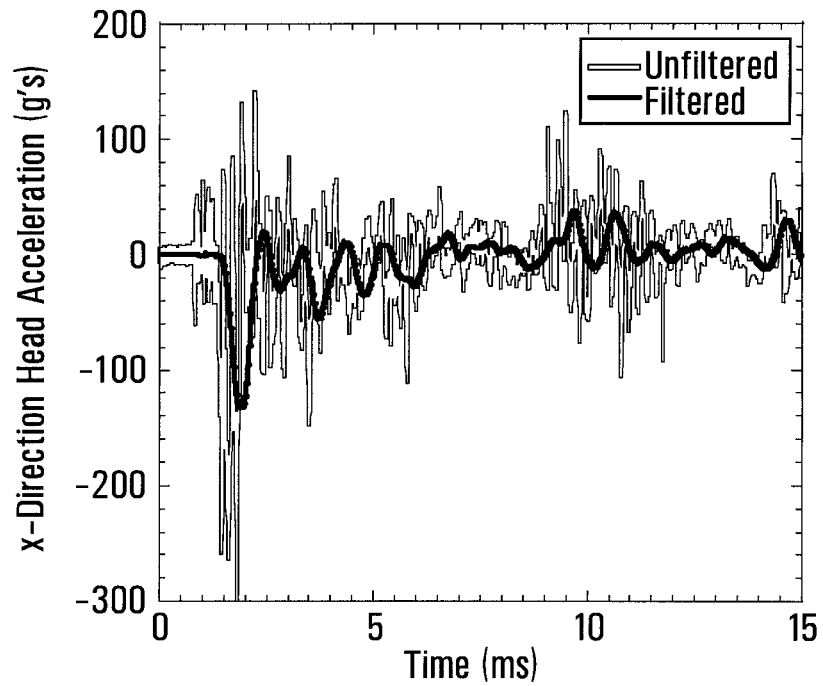
FIG. 8 shows an example of both unfiltered and filtered head acceleration traces in the x-direction (front-back) of a forward facing mannequin towards an explosion at a standoff distance of 3 meters, provided by 8.5 pounds of C4.
Figure 9:
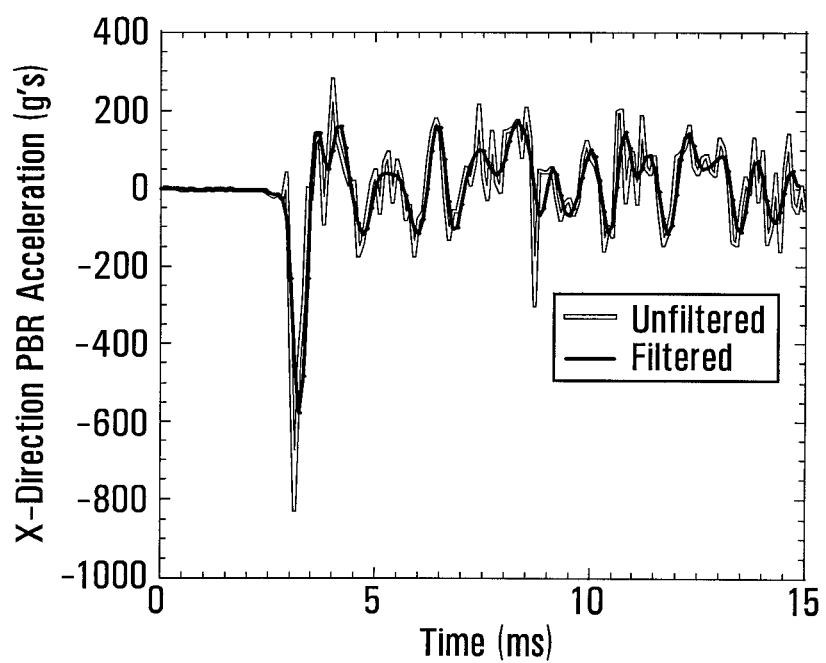
FIG. 9 shows an example of unfiltered and filtered x-direction helmet acceleration traces as recorded by a data recording unit from a forward-facing mannequin during the explosion of FIG. 8.

The earliest stages of a blast event are critical in determining potential injury as this is when the maximum acceleration(s) occur. Typically, a subject is exposed to maximum acceleration values in the first few milliseconds of a blast event, for example, the first one or two milliseconds. The largest acceleration impulses are usually the first to arrive, and these initial impulses may only last one or two milliseconds. An example of the acceleration of the head of an anthropomorphic mannequin measured during a blast event is shown in FIG. 8. In this example, the mannequin's head is facing forwards towards the blast which is generated by a charge containing 8.5 pounds of C4 at a distance from the mannequin of 3 meters. The graph shows two x-direction (front-back) acceleration traces, one being an unfiltered trace and the other being filtered by a band pass filter which cuts off frequencies above about 1,650 Hertz. As can be seen, the peak acceleration occurs at about 0.5 milliseconds or 500 microseconds after the point at which the acceleration first begins to change. This peak acceleration only lasts for about 1 millisecond. FIG. 9 shows an example of filtered and unfiltered x-direction acceleration traces from the same blast event as that of FIG. 8, as measured by a data recording unit mounted to a helmet fitted on and secured to the mannequin's head. Again, the peak acceleration occurs within the first 500 microseconds and has a duration of about 1 millisecond. As described below, embodiments of the data recording unit are capable of switching from an inactive to an active state in response to acceleration measured by the sensors in a sufficiently short time to enable at least part of the earliest acceleration impulse, which may be the strongest, to be recorded.

When an event of interest occurs, such as an impact event or a blast event, as determined by the acceleration measured by one or more accelerometers reaching or exceeding the threshold value, a trigger signal 131 is output from the control circuit 119 and causes the data processing unit 117 to turn on and start recording. The threshold value may be set at about 50 gs, for example, or any other suitable value. In some embodiments, the data processing unit is triggered to start by an acceleration from any one or more of the acceleration sensors which exceeds a pre-set threshold. In some embodiments, the acceleration trigger threshold is set slightly below levels where injury is expected to occur. Advantageously, this provides sufficient time for the data processing unit to start up and capture the relevant acceleration waveforms. The data processing unit may employ a rapid start up system to jump from a deep sleep mode to full execution mode in a relatively short time, for example, about 100 microseconds.

Although in some embodiments, activation of the data processing unit may be controlled by switchably connecting the data processing unit to the power source, other embodiments of the data recording unit use one or more other techniques for rapid startup, an example of which controls startup through the main CPU clock. In one embodiment, the frequency of the main clock 132 can be varied between one or more operating frequencies, for example, 5.5 MHz (or any other suitable frequency) and a frequency of 0 Hz, for example. This may be implemented by switching the clock between ON and OFF states, for example in response to the trigger signal 131 from the control circuit 119. In one embodiment, the clock may comprise a solid state oscillator rather than a crystal oscillator to enable the clock to start quickly, for example in one or two clock cycles, which for a clock frequency of 5.5 MHz would take about 0.2 to 0.4 microseconds. When the main clock is in the OFF state, the CPU effectively sees that the clock has stopped, ceases to execute the current instruction and holds its current state. Although power to the data processing unit is available, power is conserved when the data processing unit is in the "inactive" state, and execution of instructions is suspended.

On receiving a trigger or control signal from the control circuit 119, the clock turns ON and provides a clocking signal to the data processing unit which, in response, becomes active and begins to execute instructions. Advantageously, controlling the data processing unit between active and inactive states using the main clock rather than switchably ON/OFF coupling the data processing unit to the power source reduces the amount of power required to activate the data processing unit.

In some embodiments, power for activating or driving the main CPU clock is provided both by the control signal 131 and the data processing unit. In a specific embodiment, the trigger signal lasts for a sufficient time to power the clock on until power for the clock can be supplied by the data processing unit. Any suitable means may be provided to maintain the control or trigger signal 131 at an appropriate level to provide power to the clock for a sufficient period of time until the data processing unit has started and can provide power to the clock. The means may for example be provided by an appropriate filter. In some embodiments, once the data processing unit receives an appropriate clocking signal from the main clock, the data processing unit executes a relatively short "house-keeping" program, which may include an instruction to provide power to the main clock. Once active, the data processing unit is able to receive and convert analog accelerometer signals to digital signals and record the digital signals.

In some embodiments, the data recording unit is adapted to record data for a predetermined length of time, for example, any time from about 1 to 15 milliseconds or any other suitable time, e.g. a length of time that is sufficient to record the maximum acceleration only or the latter plus a predetermined additional time. The data processing unit may also be adapted to maintain itself in the active state for a predetermined period of time and then cause itself to change to an inactive state to conserve power. This may be implemented, for example, by configuring the data processing unit to turn off power to the clock a predetermined period of time after the CPU becomes active. Once in the inactive state, the data processing unit remains in that state until another acceleration event causes the data processing unit to change to the active state.

In the present embodiment, the analog waveform from each sensor is converted by a respective A to D converter to a digital signal and stored in the first, volatile memory unit 139. The A to D converters may be adapted to operate at any desired sampling rate, for example, 10 kHz or any other suitable frequency. The band pass filters may be configured to ensure that the signals to the A to D converters do not fluctuate faster than half the A to D sampling frequency to reduce frequency and amplitude errors in the digitized waveforms. Each of the first, second and third A to D converters may be adapted to convert simultaneously so that the direction of each instantaneous acceleration can be determined efficiently. When an event occurs in which the acceleration is sufficient to activate the data recorder, acceleration data is received by the first memory unit and recorded therein with the time of the event, as provided by the real time clock 159, and the temperature from the temperature sensor 143. After capturing an event in the first memory unit 139, the data processing unit may be adapted to make a decision either to store or not to store the data in non-volatile memory, based, for example, on the measured acceleration. Such a determination may be made based on whether a peak acceleration exceeds an injury threshold or not. The data recording unit may be provided with one or a plurality of such threshold(s). The threshold(s) may be set by an external computer, via a suitable interface, for example, interface 151. In one embodiment, a threshold may be set at 100 gs, for example, or any other suitable value.

If the decision by the data processing unit is to retain the data stored in the volatile memory 139, data is then transferred from the volatile memory to the non-volatile memory unit 141, where the data may be stored indefinitely without requiring electrical power. Once the data has been transferred from the first to the second memory unit, the data processing unit shuts itself down, entering a "sleep" state, and waits for the next event. If the data processing unit decides not to keep the event data, the data processing unit shuts itself down without transferring the event data to non-volatile memory, resulting in the loss of the data recorded in the volatile memory 139.

As described above, the data recording unit may be adapted to enable electrical power to one or more of the acceleration sensors and/or the data processing unit to be turned on or off to extend battery life. This feature may be used to prolong battery-shelf-life so that the unit can be activated only when it is brought into service rather than during periods of storage or non-use. For this purpose, the data recording unit may include a switch which may be manually accessible on the device or a switch (e.g. power management module 163, 164) accessible via a communications port or interface, for example interface 151. In this latter case, an external control signal may cause the switching module 163, 164 to change state from OFF to ON and the switching module may be adapted to maintain itself in the ON-state thereafter without further application of the control signal. Electrical power to the unit may be switched off in a similar manner.

Electrical power may be provided to the data recording unit other than via the batteries to enable the data processing unit to be turned on and data downloaded from the internal non-volatile memory 141 and/or the external memory 157. Advantageously, this feature allows data to be retrieved in the event that the batteries no longer have sufficient energy to activate the unit for this purpose.

Memory Management

As described above, in the present embodiment, memory associated with the data recording unit includes a first memory unit 139 for receiving and recording data from the A to D converters, a second memory unit 141 for receiving and storing data from the first memory unit, and an external memory unit 157. In some embodiments, the first memory unit comprises a random access memory to capture and store high speed samples from the A to D converters and to keep the data until a decision has been made as to whether to save it. To reduce power consumption, data which is to be saved is transferred to the second, non-volatile memory unit. The second memory unit 141 may have the capacity to store simultaneously event data from a number of separate events. In some embodiments, data stored in the second memory unit may be transferred to the external memory unit 157. In some embodiments, data from a number of separate events may be transferred from the second memory unit 141 to the external memory unit 157 in a single or the same write operation to reduce the power which would otherwise be required if data from each event is transferred in separate, discrete write operations. In some embodiments, the data processing unit is adapted to control the transfer of data from the second memory unit to the external memory unit once a predetermined number of events have been recorded in the second memory unit. In one embodiment, the data processing unit may be arranged to transfer data only when more than three, for example, ten events have been accumulated and to transfer those (ten) events in a single write operation. In other embodiments, the number of accumulated events prior to transfer may be any other number and the number of events transferred in a single write operation may also be any other number, and not necessarily the same number as the number of accumulated events. Preferably event data for more than one event is transferred in a single write operation.

In some embodiments, the non-volatile memory comprises a solid-state memory to withstand the high forces experienced by the data recording unit. The amount of memory may be limited to conserve electrical power, reduce size and save weight. The non-volatile memory of the data processing unit may comprise a flash memory, for example, an electrically erasable programmable read-only memory (EEPROM), and may be used to store firmware and accumulate data from a plurality of events before the data is archived to the external memory. The external memory may also comprise a solid state flash memory.

In some embodiments, other data may be stored in one or more of the available memories. This may include data which is specific to the data recording unit to enable the data recording unit to operate and/or recorded data to be processed. The data may include offset value(s) for the acceleration sensor(s). For example, a sensor may provide a non-zero output in the absence of any acceleration. Offset values may be used by the control circuit 119 to modify/correct the threshold value that controls activation of the data processing unit, and/or to modify/correct threshold values used to determine whether to keep the recorded data or not. The values may include multiplication factor(s) resulting from any signal amplifiers, or other conditioning. The data may be available to be output to an external device via a suitable interface for subsequent use, which may include correcting/adjusting recorded data for analysis and/or other processing. Storing such values in or with the unit is particularly convenient, as it obviates the need for the values to be stored elsewhere, for example in a central database, their associated input thereto, which may be prone to error, and their maintenance therein.

Sensors

In addition to acceleration sensors, the data recording unit may include a temperature sensor. The temperature sensor may be included in the data processing unit or may be separate therefrom. Since the accelerometer sensors may exhibit some temperature dependence, providing a temperature sensor enables temperature compensation to be performed on the data to improve accuracy of the measurement, if required.

Embodiments of the data recorder may include a communication port for enabling data to be downloaded to an external device. The port may be one which requires a physical wireline connection. In some embodiments, the data recorder may include a wireless interface for communicating with an external device to enable, for example, data to be downloaded using a wireless connection. In some embodiments, the protocol used for transferring data may enable secure data transfer over short ranges with efficient, low power operation. The protocol may be based on the IEEE 802.15.4 Standard for the physical and media access control layer, an example of which is known as ZIGBEE. The protocol may also allow data to be downloaded from a number of separate data recording units.

Embodiments of the data recording unit may include an optional indicator, which may comprise a visual indicator such as a red or green light or both to indicate if power to the unit is turned on, thereby confirming that the unit is ready to record events.

Figure 10:
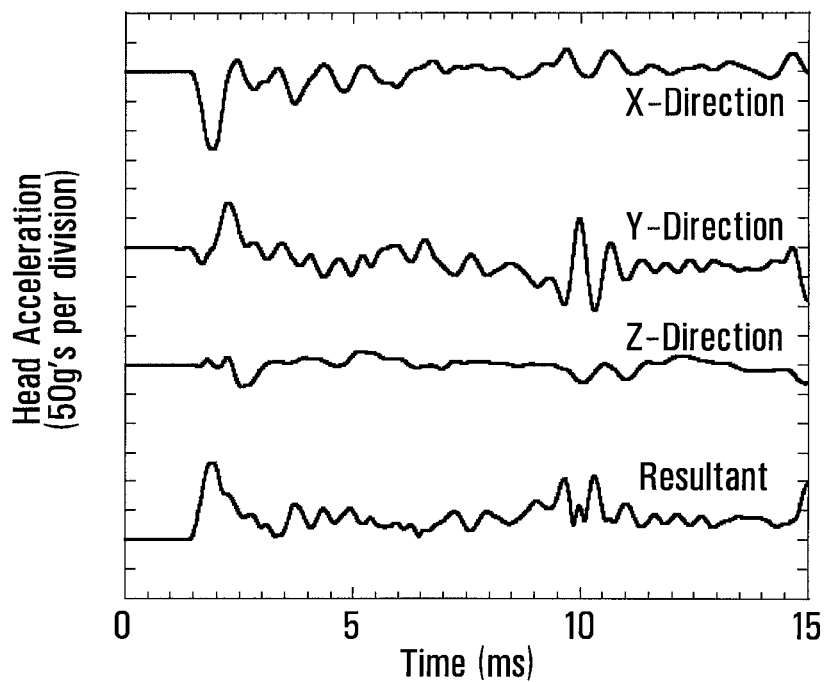
FIG. 10 shows an example of filtered head acceleration traces for x, y (left-right) and z (up-down) directions, and the resultant acceleration trace for the same forward-facing mannequin and explosion of FIGS. 8 and 9.

FIG. 10 shows an example of filtered acceleration traces for the x, y and z directions measured by accelerometers mounted in the head of a mannequin together with the resultant acceleration trace derived from the x, y and z direction acceleration traces. The measurements were made during the same blast event of FIGS. 8 and 9, i.e. with the mannequin's face facing forward towards an 8.5 pound C4 charge at a distance of 3.0 meters. As can be seen, the peak of the resultant acceleration experienced by the mannequin's head occurs within the first 1 or 2 milliseconds of the blast.

Figure 11:
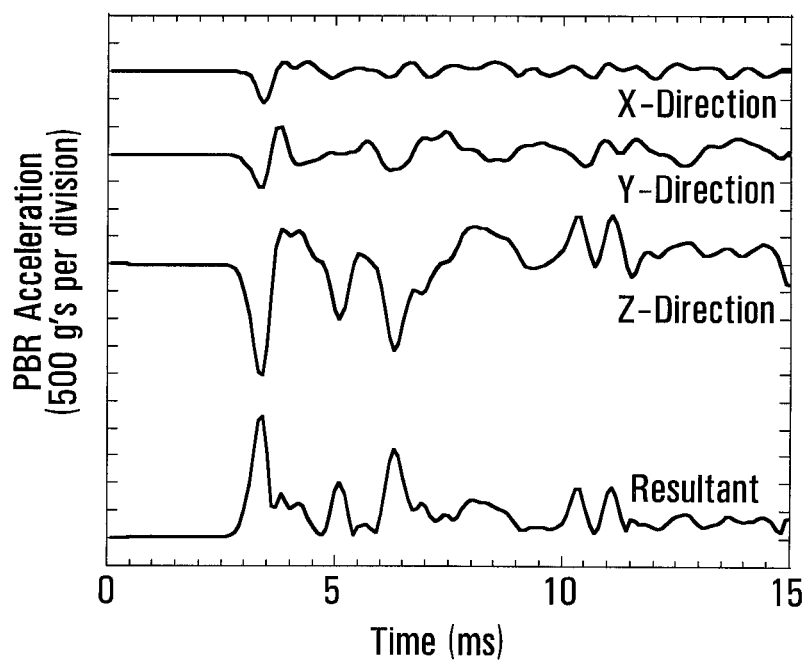
FIG. 11 shows examples of x, y and z direction, filtered acceleration traces and a resultant acceleration trace as measured by a helmet-mounted data recording unit for the same forward-facing mannequin and blast event of FIGS. 8 to 10.

FIG. 11 shows filtered acceleration traces in the x, y and z directions as measured by an embodiment of a data recording unit mounted to a helmet and worn by and secured to the mannequin's head for the same blast event as FIGS. 8 to 10, together with the resultant acceleration trace derived from each of the measured x, y and z acceleration traces. Again, the peak acceleration or accelerations of the helmet occur within the first one or two milliseconds of the blast. The magnitude of the peak acceleration of the helmet is higher than the peak acceleration of the mannequin's head. This is at least partly due to the mechanical decoupling between the head and helmet provided by the resilient or flexible helmet suspension or cushioning system, which allows relative movement between the head and helmet, and the difference in mass between the head and helmet. In practice, for head acceleration monitoring, acceleration may be measured by helmet mounted accelerometers only. In order to derive head acceleration from a helmet mounted data recording unit, calibration tests may be performed in order to determine a relationship describing or defining the correlation between helmet and head accelerations. Such a determination may be made by performing a number of measurements with the head/helmet combination subjected to different blast strengths, which may be varied, for example, by either changing the strength of the blast or the distance between the explosive and the mannequin.

Figure 12:
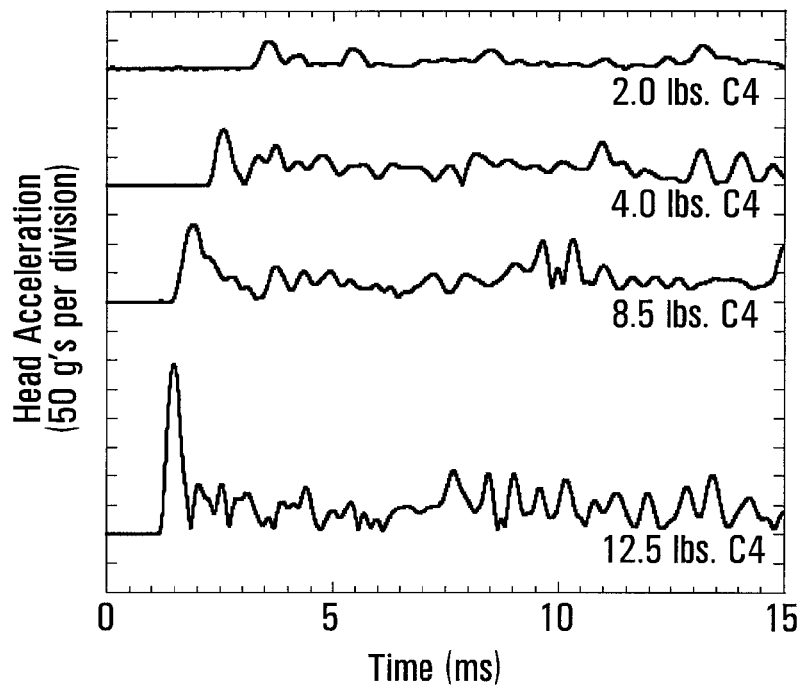
FIG. 12 shows resultant, filtered head acceleration traces for a forward-facing mannequin during 2.5 pounds, 4.0 pounds, 8.5 pounds and 12.5 pounds of C4 charges at a standoff distance of 3 meters.
Figure 13:
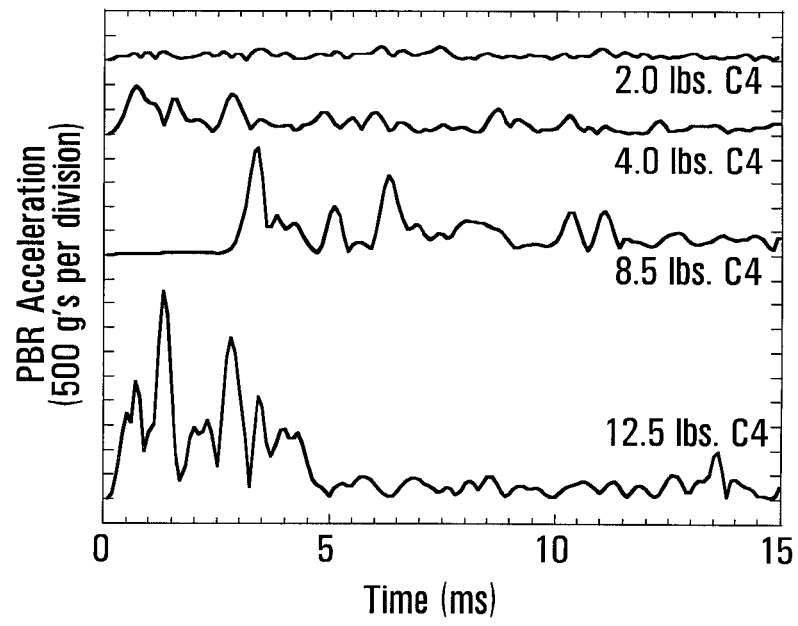
FIG. 13 shows an example of resultant filtered acceleration traces as measured by a helmet mounted data recording unit for the forward-facing mannequin of FIG. 12 during the 2.0 pounds, 4.0 pounds, 8.5 pounds and 12.5 pounds C4 charges at a standoff distance of 3 meters.

FIGS. 12 and 13 show resultant acceleration traces for head and helmet accelerations, respectively, measured for four blast events using different quantities of explosive at the same standoff distance of 3 meters. In determining the correlation between head and helmet accelerations, the peak (or other value of) acceleration may be obtained from each acceleration trace and the ratio between peak head and peak helmet accelerations may be determined. A mathematical expression may then be fitted to the data, thereby establishing a relationship between head and helmet accelerations. This relationship may then be used when analyzing data from the data recording unit to determine head acceleration. This data may be used to determine a level of injury that may have been caused by the blast event. For example, previous studies carried out by the applicant, in which anthropomorphic mannequins have been subjected to the blast of high explosives in free field (no obstacles) conditions, have indicated that the blast-induced head acceleration injury threshold corresponds to a peak resultant head acceleration of the order of 450 gs.

Figure 14:
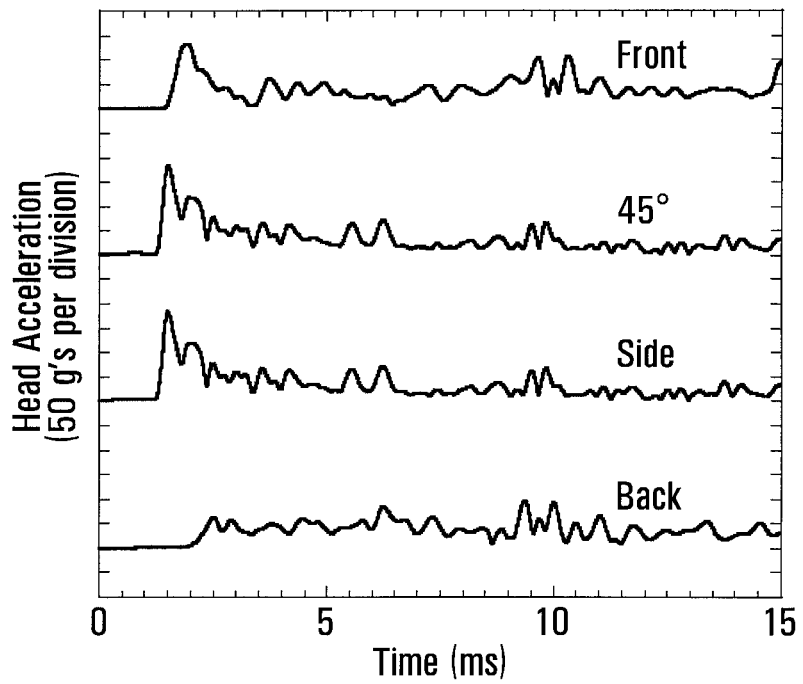
FIG. 14 shows an example of resultant, filtered head acceleration traces for a mannequin oriented in different directions with respect to 8.5 pound, C4 charges at a standoff distance of 3 meters.

The inventors have found that both head and helmet acceleration depend on the orientation of the head/helmet combination relative to the source of the blast. In addition, the inventors have found that the ratio between head acceleration and helmet acceleration may also depend on the orientation of the head/helmet combination relative to the source of the explosion. FIG. 14 shows examples of resultant head acceleration traces measured for four different mannequin orientations: (1) the front of the mannequin faces the explosive source; (2) the back and side of the mannequin are directed towards the explosive source, with a line extending between front and back of the mannequin at 45° to the source; (3) the side of the mannequin is directed towards the explosive source; and (4) the back of the mannequin is directed towards the explosive source. As can be seen from the traces, the peak acceleration varies depending on the orientation, with the highest peak acceleration values resulting from the side and 45° orientations and the lowest peak acceleration values resulting from the back orientation.

Figure 15:
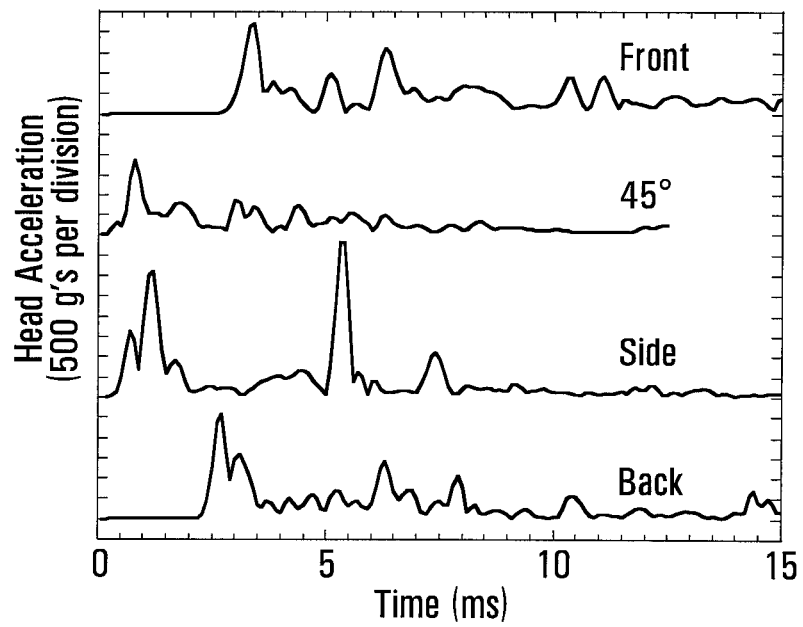
FIG. 15 shows examples of acceleration traces as measured by a helmet mounted data recording unit for the mannequin of FIG. 14 at different orientations with respect to the explosive charge.

FIG. 15 shows resultant acceleration traces measured by a helmet mounted data recording unit for the same orientations and blast events of FIG. 14. As can be seen, the highest acceleration value results from a side orientation, the second highest acceleration results from the back orientation, the third highest results from front orientation and the lowest acceleration peak results from the 45° orientation. This shows that the ratio between head and helmet acceleration varies depending on the orientation of the head relative to the explosive source. The relationship between head and helmet acceleration may be determined for any number of different orientations and subsequently used to determine head acceleration from data recorded by the helmet mounted data recording unit. For example, the acceleration traces measured by the accelerometers of the data recording unit provide the direction of the blast relative to the head/helmet combination from which the orientation of the helmet relative to the explosive source can be determined. The orientation value can then be used to look up a value of the ratio or other relationship between head and helmet acceleration and the ratio or other relationship then used to determine head acceleration from the value of acceleration measured by the data recording unit. The determined head acceleration value may then be used to determine whether or not an injury has occurred and possibly the level of injury.

In other embodiments and aspects of the invention, any feature disclosed herein may be omitted altogether or substituted by another feature which may or may not be an equivalent or variant thereof. For example, in some embodiments, the z-direction accelerometer may be omitted. This may be appropriate if the azimuthal direction of acceleration (i.e. the direction in the horizontal plane) only is of interest.

Embodiments of the data recorder may be mounted on any object. For example, it may be mounted on a vehicle or a stationary object, or on any article of appareil to be worn by a person.

Embodiments of the data recorder may be capable of measuring accelerations having values of at least 1,500 gs, for example, 5,000, 10,000 or 15,000 gs or more.

Other aspects and embodiments of the invention comprise any feature disclosed herein in combination with any one or more other feature disclosed herein or a generic or specific equivalent or variant thereof.

Any embodiment may comprise sensor means for measuring rotational motion, for example, rotational acceleration. The sensor means may comprise a plurality of spaced apart sensors (e.g. accelerometers) located at different positions either within a data recording unit, or one or more sensors may be separate from the unit and mounted on the object to be monitored, for example, on a head protector.

The data recording unit may record data from the rotational sensor(s). Recording and storing the data may be performed using the same or similar methodology to that disclosed herein in relation to the axial acceleration data.

Numerous modifications to the embodiments described above will be apparent to those skilled in the art.

The invention claimed is:

1. An apparatus for measuring acceleration of a person's head or other object, comprising sensing means for sensing acceleration, and a controller for controlling recording of data resulting from the sensed acceleration, wherein the controller is adapted to determine whether or not to enable recording of the data based on the sensed acceleration, and further comprising data receiving means for receiving sensed acceleration data from the sensing means, the receiving means requiring electrical power to enable the data to be received thereby, and wherein said controller causes electrical power to said receiving means to be controlled based on the sensed acceleration;
   wherein said controller is adapted to enable recording of the data if the sensed acceleration meets a predetermined criteria;
   wherein said predetermined criteria comprises one of (1) the sensed acceleration reaches a predetermined value and (2) the sensed acceleration exceeds a predetermined value;
   wherein said predetermined value is a value above zero and below a value that would or is likely to cause a predetermined injury to a person; and
   wherein said predetermined value is selected to provide sufficient time for said receiving means to change from an inactive state to an active state to receive one or both of (1) data indicative of the maximum acceleration associated with an event and (2) acceleration data indicative of an injury.

2. An apparatus as claimed in claim 1, wherein said receiving means comprises any one or more of signal conditioning means for conditioning the signal, an analog to digital converter, a processor and a memory.

3. An apparatus as claimed in claim 2, further comprising a second memory operatively coupled to said first memory for receiving data therefrom.

4. An apparatus as claimed in claim 3, further comprising determining means for determining whether or not to transfer data from said first memory to said second memory based on said acceleration data.

5. An apparatus as claimed in claim 4, wherein said determining means is adapted to cause said data to be transferred from said first memory to said second memory if said acceleration data meets a predetermined criteria.

6. An apparatus as claimed in claim 5, wherein said predetermined criteria is that a value of acceleration in said acceleration data is likely to be sufficient to cause injury or has been previously determined to cause injury.

7. An apparatus as claimed in claim 5, further comprising a third memory operatively coupled to said second memory for receiving data therefrom.

8. An apparatus as claimed in claim 7, further comprising a memory controller for controlling the transfer of data from said second memory to said third memory, wherein said memory controller is conditioned to transfer acceleration data from said second memory to said third memory only if said second memory contains acceleration data from a plurality of separate events.

9. An apparatus for measuring acceleration of a person's head or other object, comprising sensing means for sensing acceleration, and a controller for controlling recording of data resulting from the sensed acceleration, wherein the controller is adapted to determine whether or not to enable recording of the data based on the sensed acceleration, and further comprising data receiving means for receiving sensed acceleration data from the sensing means, the receiving means requiring electrical power to enable the data to be received thereby, and wherein said controller causes electrical power to said receiving means to be controlled based on the sensed acceleration;

further comprising monitoring means for monitoring the time of an acceleration event and means for recording acceleration data of an event and the time of the event; and wherein said sensing means comprises a plurality of sensors each capable of measuring acceleration in a single direction and configured to measure acceleration in a direction which is mutually perpendicular to the direction of one or more other acceleration sensors.

10. An apparatus as claimed in claim 9, wherein said controller comprises a plurality of comparators each for comparing acceleration sensed by a respective acceleration sensor with a predetermined value.

11. An apparatus as claimed in claim 9, wherein said controller comprises a comparator for comparing the sensed acceleration with a predetermined value.

12. An apparatus as claimed in claim 11, comprising control means for controlling operation of said data receiving means, a generator for generating timing signals for operation of said control means, and wherein said controller is operatively coupled to said generator to control said generator.

13. An apparatus as claimed in claim 12, wherein said generator is adapted to switch from an inactive state to an active state in response to said controller determining to enable recording of the data based on the sensed acceleration.

14. An apparatus as claimed in claim 12, wherein said control means is adapted to switch said generator from an active state to an inactive state after said generator has been in the active state for a predetermined period of time.

* * * * *